US005939555A

United States Patent [19]

Foguet et al.

[11] Patent Number: 5,939,555

[45] Date of Patent: Aug. 17, 1999

[54] POLYMORPHS B AND C OF 1-[2,4-DICHLORO-β-[(7-CHLOROBENZO[B]THIEN-3-YL)METHOXY]PHENETHYL]IMIDAZOLE MONONITRATE

[75] Inventors: Rafael Foguet; Lluis Anglada; Jose A. Ortiz; Aurelio Sacristan; Josep Maria Castello; Manuel Mauricio Raga, all of Barcelona, Spain

[73] Assignee: Ferrer Internacional, S.A., Barcelona, Spain

[21] Appl. No.: 08/702,536

[22] PCT Filed: Jan. 4, 1995

[86] PCT No.: PCT/ES95/00001

§ 371 Date: Oct. 21, 1996

§ 102(e) Date: Oct. 21, 1996

[87] PCT Pub. No.: WO96/20939

PCT Pub. Date: Jul. 11, 1996

[51] Int. Cl.[6] ...................... C07D 233/02; C07D 233/04; C07D 233/54; A61K 31/415

[52] U.S. Cl. ...................... 548/311.1; 424/401; 424/433; 514/397

[58] Field of Search .......................... 548/311.4; 514/397

[56] References Cited

U.S. PATENT DOCUMENTS 5,135,943 8/1992 Foguet et al. .......................... 514/397

FOREIGN PATENT DOCUMENTS 2376856 4/1978 France .

OTHER PUBLICATIONS

Arneimittel–Forschung Drug Research, vol. 42, No. 5A, 1992 DE, pp. 695–698 Albet et al.

Pharmaceutical Anal., vol. 117, 1992, p. 449.

*Primary Examiner*—Floyd D. Higel

*Attorney, Agent, or Firm*—Birch, Stewart, Kolasch & Birch, LLP

[57] ABSTRACT

Two polymorphs of 1-[2,4-dichloro-β-[(7-chloro-benzo[b] thien-3-yl)methoxy]phenetyl]imidazole mononitrate have been identified. A process for the preparation thereof and composition are described.

2 Claims, 9 Drawing Sheets

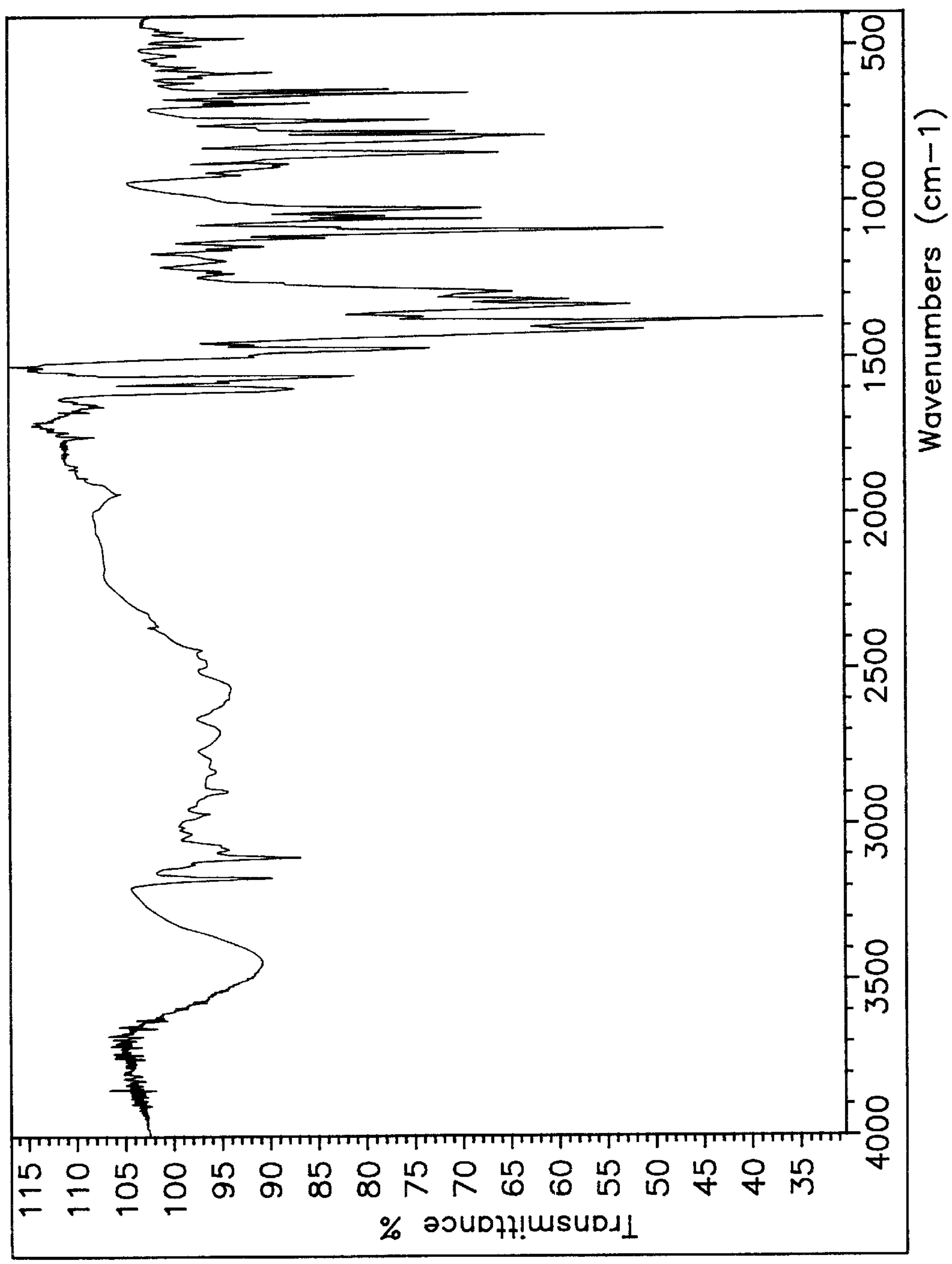
FIG. 1: IR spectrum of Sertaconazole mononitrate polymorph B (Lot Pol.B1)

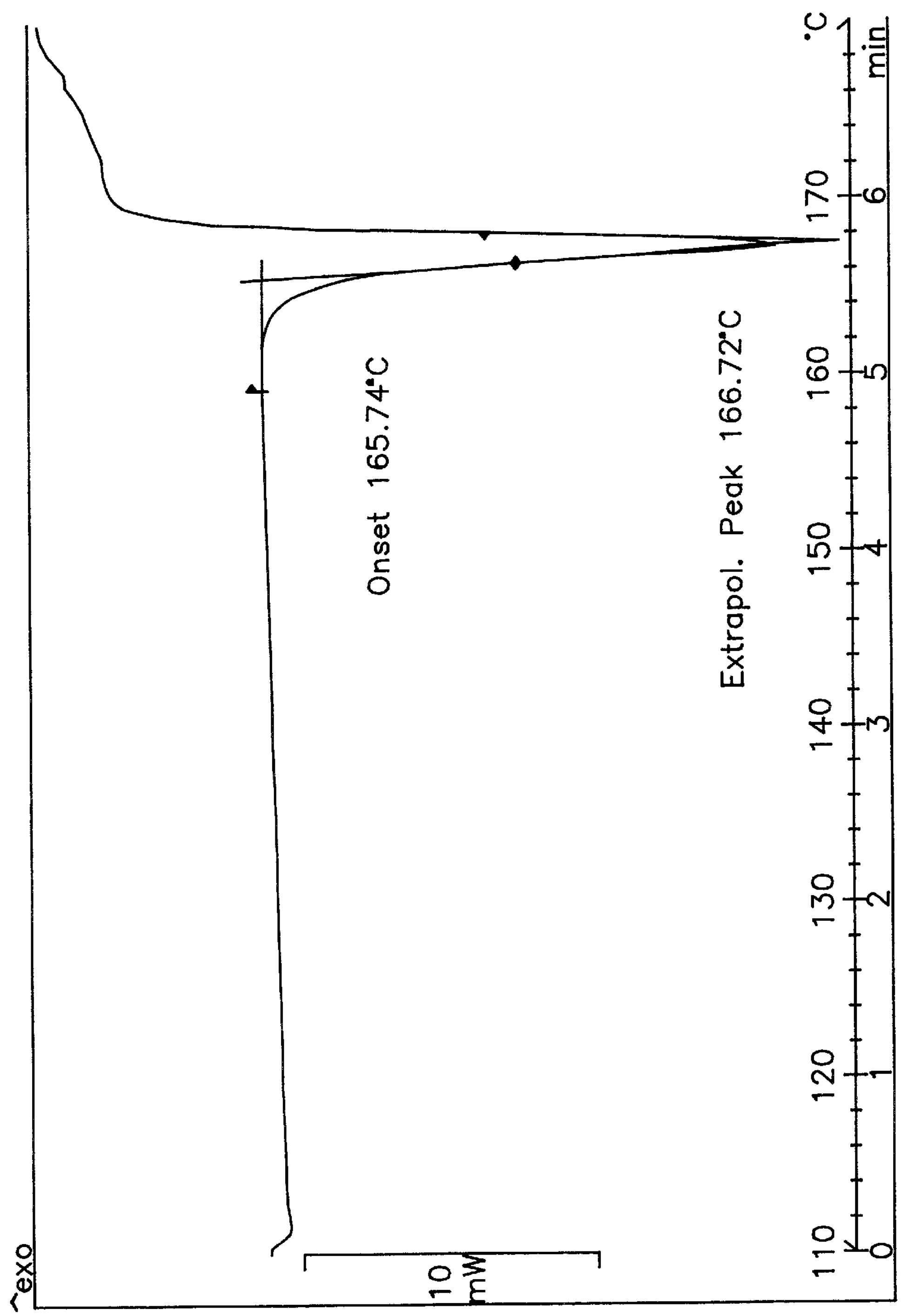
FIG. 2: Differential Scanning Calorimetry (DSC) Thermogram of Sertaconazole mononitrate polymorph B (Lot X1/AN).

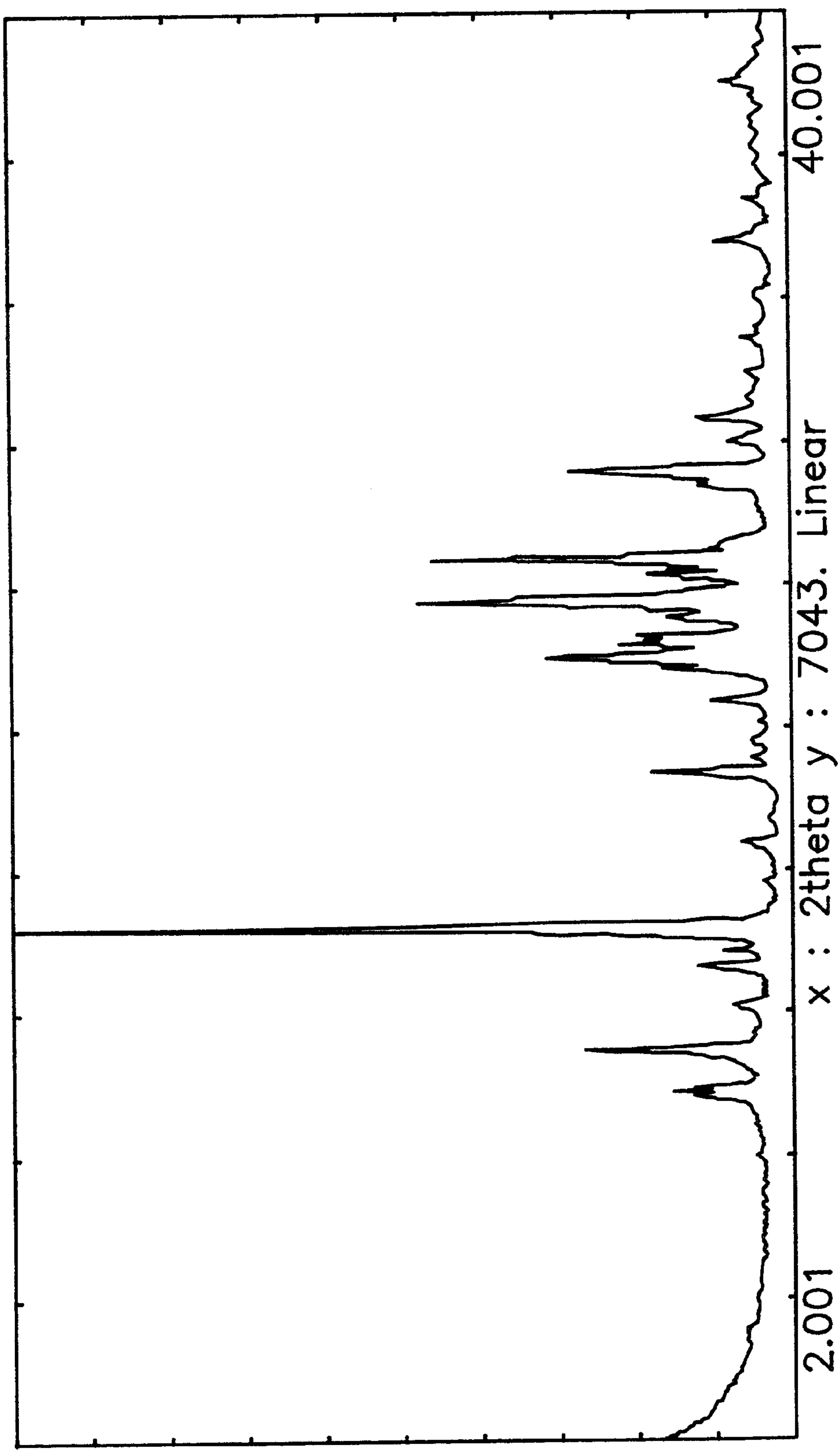
FIG. 3: X-ray Powder Diffractogram of Sertaconazole mononitrate polymorph B (Lot X1/AN)

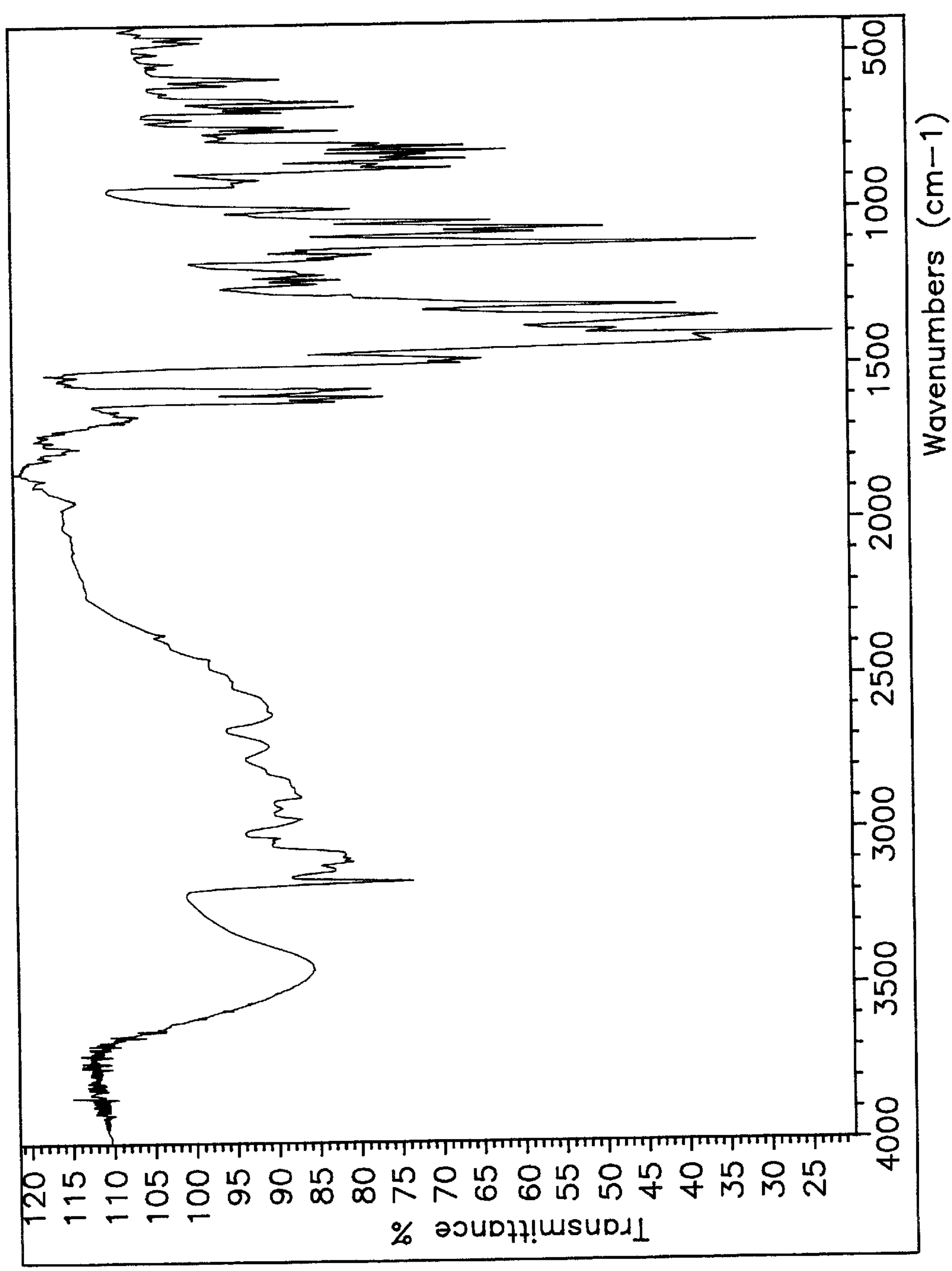
FIG. 4: IR Spectrum of Sertaconazole mononitrate polymorph C (Lot Pol.C0.1)

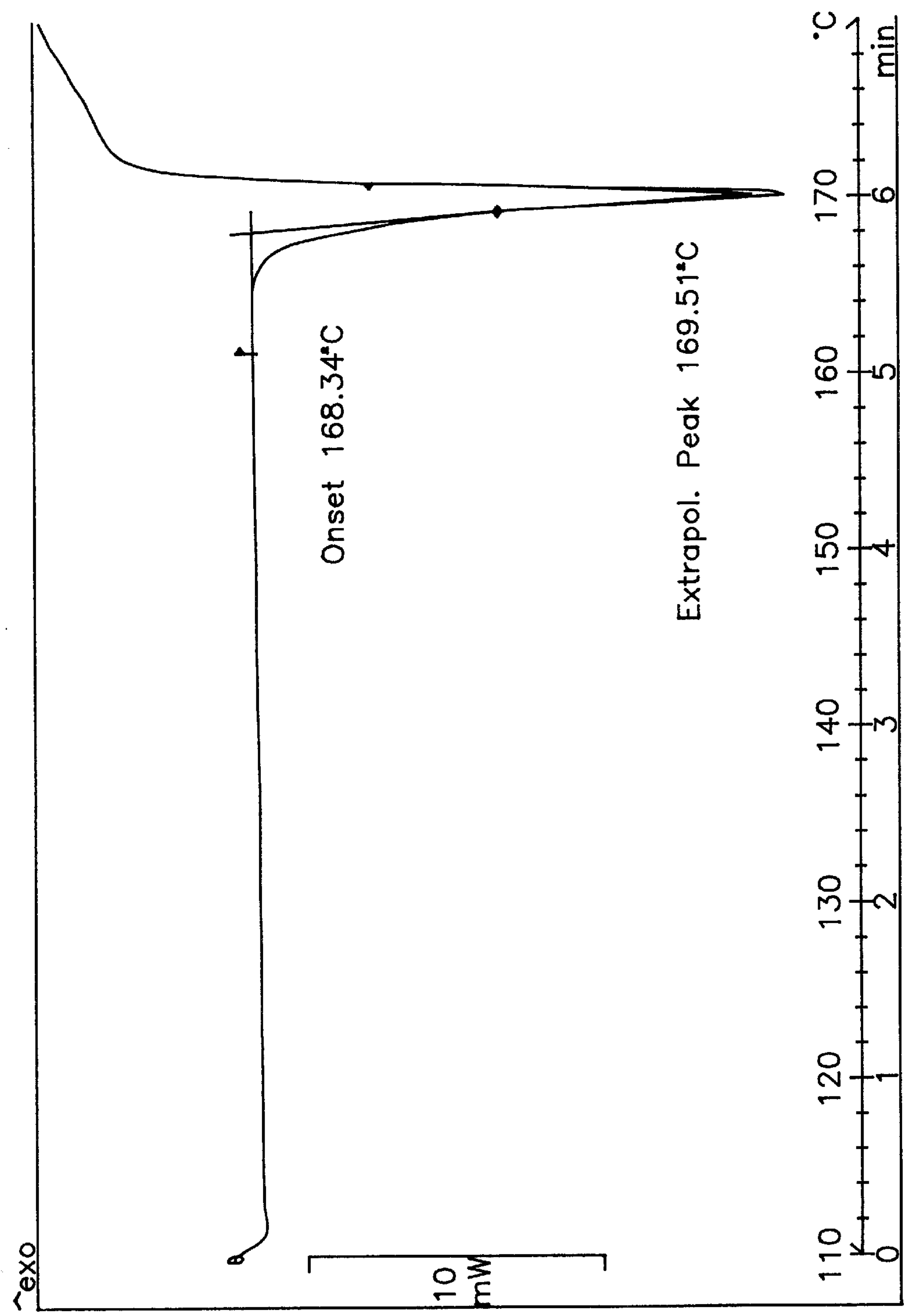
FIG. 5: Differential Scanning Calorimetry (DSC) Thermogram of Sertaconazole mononitrate polymorph C (Lot R.C13C)

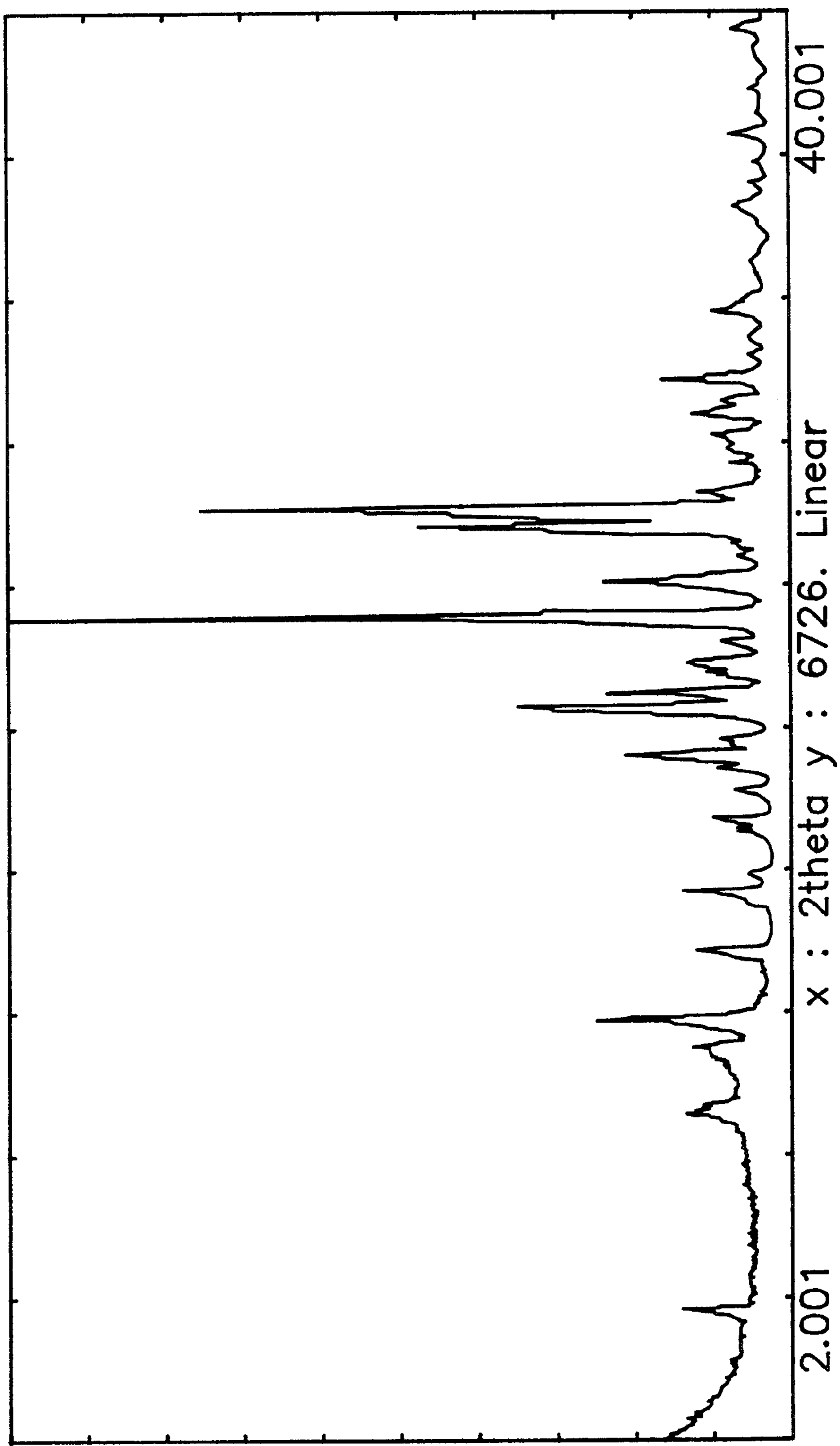
FIG. 6: X-ray Powder Diffractogram of Sertaconazole mononitrate polymorph C (Lot D-9/R-CL3CH)

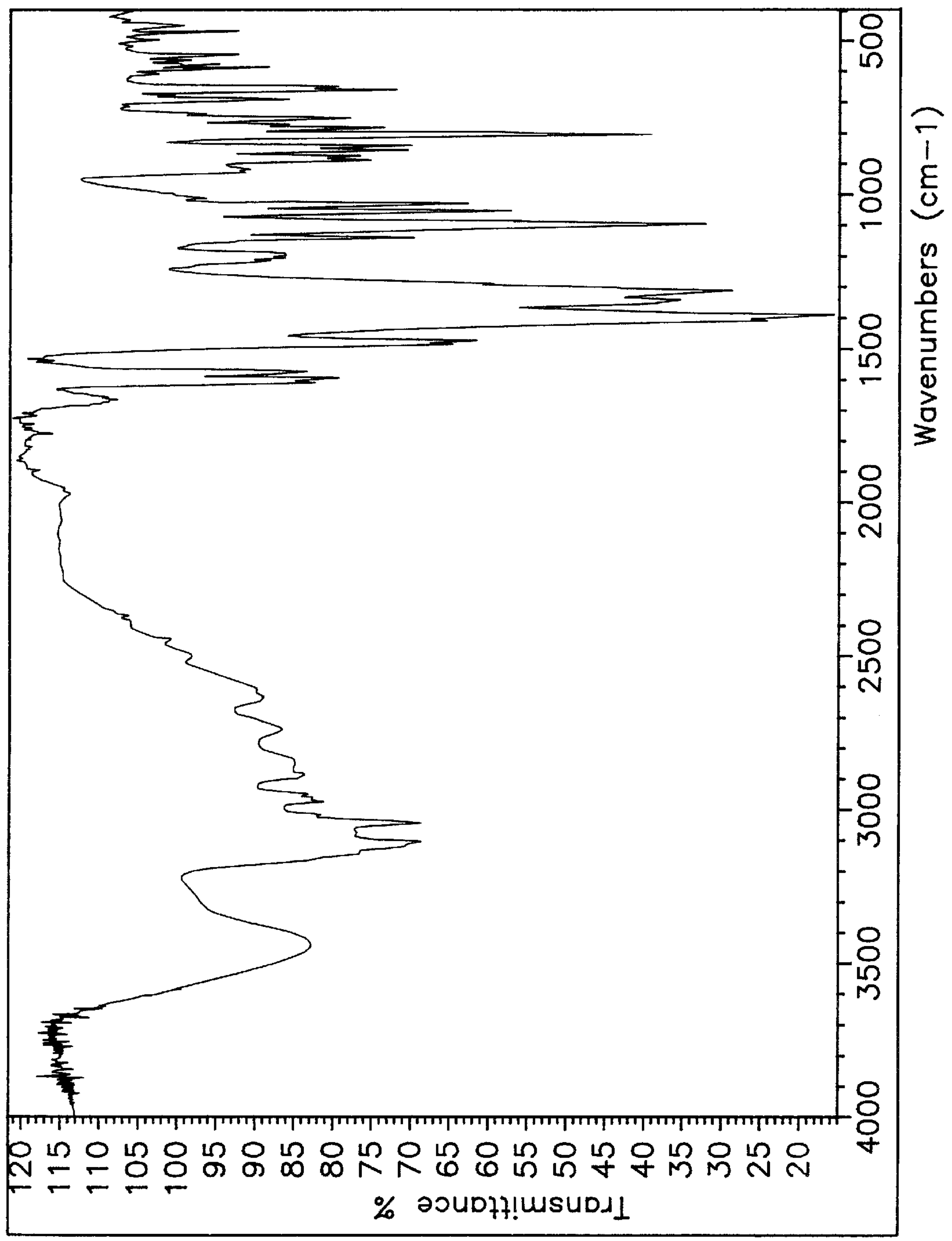
FIG. 7: IR Spectrum of Sertaconazole mononitrate polymorph A (Lot Pol.A1)

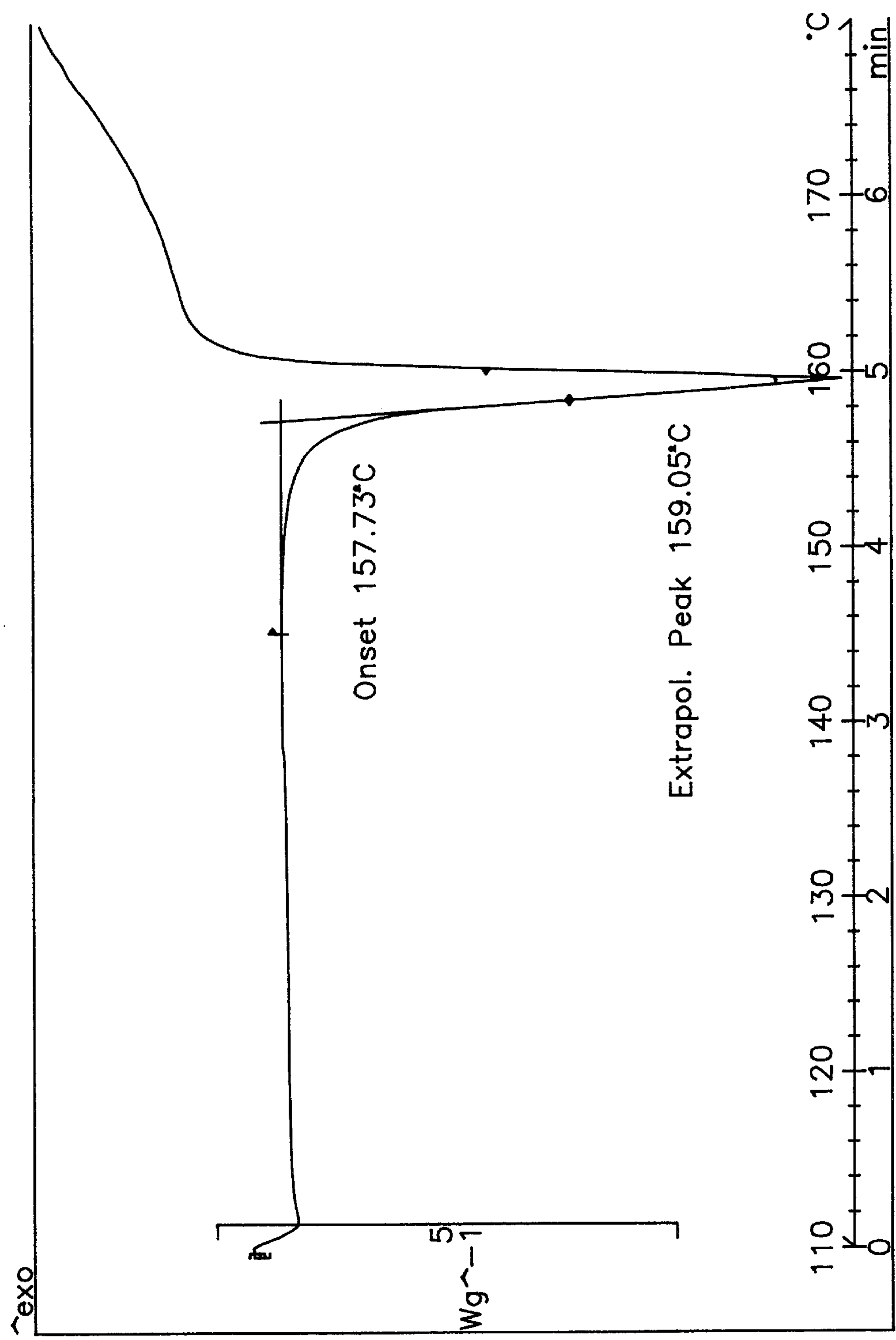
FIG. 8: Differential Scanning Calorimetry (DSC) Thermogram of Sertaconazole mononitrate polymorph A (Lot PT.B2021).

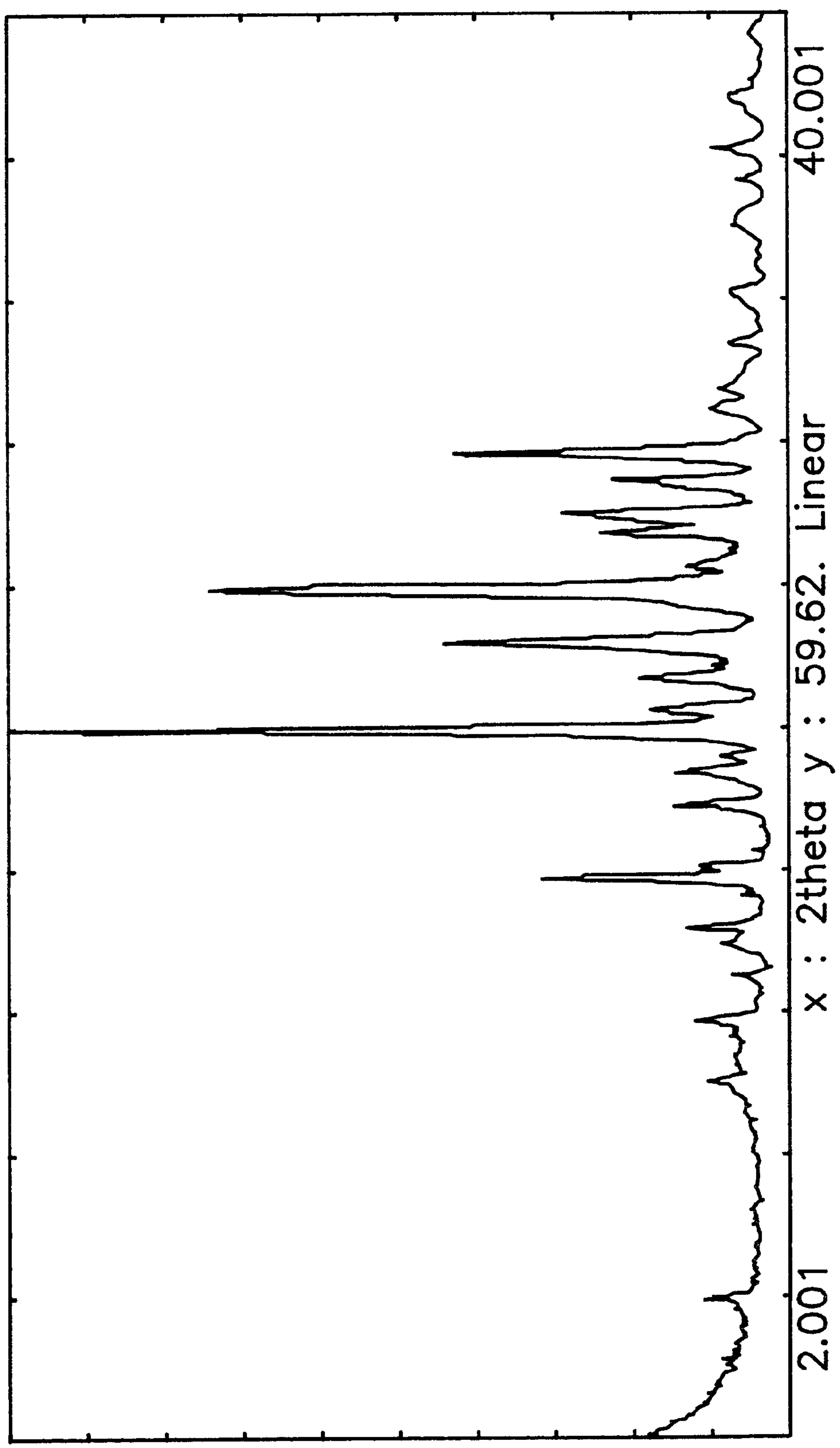
FIG. 9: X-ray Powder Diffractogram of Sertaconazole mononitrate polymorph A (Lot D7)

POLYMORPHS B AND C OF 1-[2,4-DICHLORO-β-[(7-CHLOROBENZO[B]THIEN-3-YL)METHOXY] PHENETHYL]IMIDAZOLE MONONITRATE

This application is a 371 of PCT/ES95/00001 filed Jan. 4, 1995.

The present invention relates to novel Polymorphs B and C of 1-[2,4-dichloro-β-[(7-chlorobenzo[b]thien-3-yl) methoxy]phenethyl]imidazole mononitrate-compound known as sertaconazole mononitrate (WHO).

BRIEF DESCRIPTION OF THE DRAWINGS

FIG. 1 is an infrared (IR) spectrum of sertaconazole mononitrate Polymorph B.

FIG. 2 is a differential scanning calorimetry (DSC) thermogram of sertaconazole mononitrate Polymorph B.

FIG. 3 is an X-ray powder diffractogram of sertaconazole mononitrate Polymorph B.

FIG. 4 is an infrared (IR) spectrum of sertaconazole mononitrate Polymorph C.

FIG. 5 is a differential scanning calorimetry (DSC) thermogram of sertaconazole mononitrate of Polymorph C.

FIG. 6 is an X-ray powder diffractogram of sertaconazole mononitrate Polymorph C.

FIG. 7 is an infrared (IR) spectrum of sertaconazole mononitrate Polymorph A.

FIG. 8 is a differential scanning calorimetry (DSC) of sertaconazole mononitrate Polymorph A.

FIG. 9 is an X-ray diffractogram of sertaconazole mononitrate Polymorph A.

DETAILED DESCRIPTION OF THE INVENTION

1-[2,4-Dichloro-β-[(7-chlorobenzo[b]thien-3-yl) methoxy]phenethyl]imidazole mononitrate is used in therapeutics as an antifungal agent. The preparation of this compound was disclosed in European Patent No. 0151477. The applicants have found out that sertaconazole mononitrate exhibits two novel polymorphs, B and C, which have a melting point in the range of 163–164° C. and 164.5–165.5° C. respectively. The present invention provides a process for obtaining selectively each polymorph B and C of sertaconazole mononitrate. In the aforesaid patent, sertaconazole mononitrate, which will be hereinafter referred as Polymorph A, was obtained with a melting point of 156–157° C. The applicants have found out in the course of different crystallization assays that when polymorph A is recrystallized from absolute ethanol, it yields the new polymorph B, and when polymorph A is recrystallized from chloroform, it yields the new polymorph C. The melting points of the three polymorphs are within a close range, but they are well differentiated by means of the enclosed IR spectra, DSC thermograms and X-ray powder diffractograms. FIGS. 7, 8 and 9 concerning Polymorph A are enclosed in order to support the differences between the new polymorphs B or C and primary polymorph A.

The physical properties of polymorphs B and C of sertaconazole mononitrate are different from those of primary polymorph A. In effect, polymorph B shows higher stability than that of polymorph A versus a moderate supply of external energy (such as sifting and homogenizing processes) and is, therefore, suitable for the preparation of topical dosage solid forms, such as a powder. Polymorph C is assumed to be even more stable than polymorph B versus an external energetic supply and can, therefore, be conveniently used in processes requiring a higher energetic supply, such as compression processes, thus being suitable for the preparation of tablets. In case of liquid formulations, either polymolph, B or C, can be used since the proper characteristics of a solid disappear in a solution.

In addition to the aforesaid pharmaceutical forms, polymorphs B and C of sertaconazole mononitrate mixed with pharmaceutically acceptable carriers can be administered by the oral route to humans and animals in the form of capsules, syrups, solutions, powder, etc., by an injectable route, by a rectal route, and by a vaginal-intrauterine route in the form of ovulum, ointment, cream, pessary, lotion, etc., at daily doses ranging from 100 to 800 mg; and by a topical route in the form of a cream, lotion, ointment, emulsion, solution, shampoo, gel, etc., at concentrations ranging from 0.1 to 5%.

Also polymorphs B and C of sertaconazole mononitrate in admixture with a diluent or carrier and in suspension with irrigation water can be used against crop diseases; they can also be applied by atomizing, spraying, dusting, or in the form of cream, paste, etc., at the rate of 0.1–15 kg per hectare of soil.

The following examples will illustrate the preparation of polymorphs B and C of sertaconazole mononitrate, and pharmaceutical formulations containing them. The examples are not intended to limit the scope of the invention as defined hereinabove or as claimed below.

EXAMPLE 1

Polymorph B of 1-[2,4-dichloro-β-[(7-chlorobenzo[b] thien-3yl)methoxy]phenethyl]imidazole mononitrate (Sertaconazole mononitrate polymorph B)

10 g of sertaconazole mononitrate (polymorph A) are dissolved in 100 ml of absolute ethanol at reflux. The hot solution is filtered and allowed to crystallize at room temperature without stirring. The crystalline solid formed is filtered and dried to give 8.78 g of Polymorph B of 1-[2,4-dichloro-β-[(7-chlorobenzo[b]thien-3-yl), methoxy] phenethyl]imidazole mononitrate (Sertaconazol mononitrate polymorph B).

Melting point: 163–164° C.

IR spectrum (KBr): FIG. 1

DSC thermogram: FIG. 2

X-ray diffractogram: FIG. 3

EXAMPLE 2

Polymorph C of 1-[2,4-dichloro-β-[(7-chlorobenzo[b]thien-3-yl)methoxy]phenethyl]imidazole mononitrate (Sertaconazol mononitrate polymorph C)

5 g of sertaconazole mononitrate (polymorph A) are dissolved in 150 ml of chloroform at reflux. The hot solution is filtered and allowed to crystallize at room temperature without stirring. The crystalline solid formed is filtered and dried to give 4.2 g of Polymorph C of 1-[2,4-dichloro-β-[(7-chlorobenzo[b]thien-3-yl), methoxy]phenethyl] imidazole mononitrate (Sertaconazol mononitrate polymorph C).

Melting point: 164.5–165.5° C.

IR spectrum (KBr): FIG. 4

DSC thermogram: FIG. 5

X-ray diffractogram: FIG. 6

EXAMPLE 3

| 2% powder for topical application<br>Composition for 100 g: | |
|---|---|
| Sertaconazole mononitrate polymorph B | 2 g |
| Titanium dioxide | 10 g |
| Kaolin | 10 g |
| Talc | 78 g |

EXAMPLE 4

| Vaginal tablets<br>Composition for 1 vaginal tablet: | |
|---|---|
| Sertaconazole mononitrate polymorph C | 500 mg |
| Corn starch | 90 mg |
| Aerosil 200 | 1 mg |
| Primogel | 45 mg |
| Compritol | 150 mg |
| Magnesium stearate | 7.5 mg |
| Avicel PH-101 to volume | 1100 mg |

We claim:

1. A process for the preparation of polymorph B of 1-[2,4-dichloro-beta[(7-chlorobenzo[b]thien-3-yl)methoxy] phenethyl]imidazole mononitrate having a melting point in the range of 163–164° C. which comprises dissolving polymorph A in absolute ethanol to form a solution, refluxing the solution; filtering the solution; crystallizing polymorph B at room temperature; and separating polymorph B.

2. A process for the preparation of polymorph C of 1-[2,4-dichloro-beta[(7-chlorobenzo[b]thien-3-yl)methoxy] phenethyl]imidazole mononitrate having a melting point in the range of 164.5–165.5° C. which comprises dissolving polymorph A in chloroform to form a solution, refluxing the solution; filtering the solution; crystallizing polymorph C at room temperature; and separating polymorph C.

* * * * *